US00PP20123P2

(12) United States Plant Patent
Walters

(10) Patent No.: US PP20,123 P2
(45) Date of Patent: Jun. 23, 2009

(54) ***PAPAVER ORIENBTALE* PLANT NAMED 'FLAMENCO DANCER'**

(50) Latin Name: *Papaver orientale*
Varietal Denomination: Flamenco Dancer

(75) Inventor: Chad Walters, Hudsonville, MI (US)

(73) Assignee: Walters Gardens Inc, Zeeland, MI (US)

( * ) Notice: Subject to any disclaimer, the term of this patent is extended or adjusted under 35 U.S.C. 154(b) by 181 days.

(21) Appl. No.: 11/827,336

(22) Filed: Jul. 10, 2007

(51) Int. Cl.
*A01H 5/00* (2006.01)

(52) U.S. Cl. ..... Plt./464

(58) Field of Classification Search ..... Plt./464
See application file for complete search history.

*Primary Examiner*—Wendy C. Haas

(57) ABSTRACT

The new and distinct *Papaver orientale* plant named 'Flamenco Dancer' with deeply fringed red petals, large, upright, cupped flowers on sturdy stems suitable for landscaping in mass or as a specimen plant.

2 Drawing Sheets

Botanical designation: *Papaver orientale.*
Cultivar denomination: 'Flamenco Dancer'.

BACKGROUND OF THE PLANT

The present invention relates to the new and distinct Oriental Poppy herein also referred to as, *Papaver orientale* 'Flamenco Dancer', by just the cultivar name, or as the Plant. 'Flamenco Dancer' was discovered by Chad Walters in the spring of 2002 as a chance seedling in the fields of a wholesale perennial grower in Zeeland, Mich. USA. The Plant was an uninduced mutation of *Papaver* 'Turkenlouis' (unpatented). It was then isolated and compared in subsequent years to other poppies and found to be different from all cultivars known to the discoverer.

Asexual propagation at the same nursery in Zeeland, Mich., USA by root cuttings has shown 'Flamenco Dancer' to be stable and reproduce true to type in successive generations.

SUMMARY OF THE PLANT

The Plant has not been observed in all possible environmental conditions. The phenotype may vary slightly with changes in environments such as light intensity, fertility, water availability, etc. without, however any variation in genotype.

'Flamenco Dancer' is distinct from all known cultivars in the following traits:

1. Heavily praemorse to deeply cleft and fringed petals.
2. Large deep red flowers showing basal spots on petals.
3. Compact plant habit with upward facing flowers.

Plants of 'Flamenco Dancer' could be compared to 'Turkenlouise' in that the former has a very similar plant habit and fringed praemorse petals, but 'Flamenco Dancer' has a much more intense reddish flower compared to the orange-red of 'Turkenlouise'.

BRIEF DESCRIPTION OF THE DRAWINGS

The color photographs illustrate the overall characteristics of the Plant. The colors are as true as reasonably possible given the technology available. The color values may vary slightly depending on light intensity and quality.

DETAILED BOTANICAL DESCRIPTION

Figure 1:
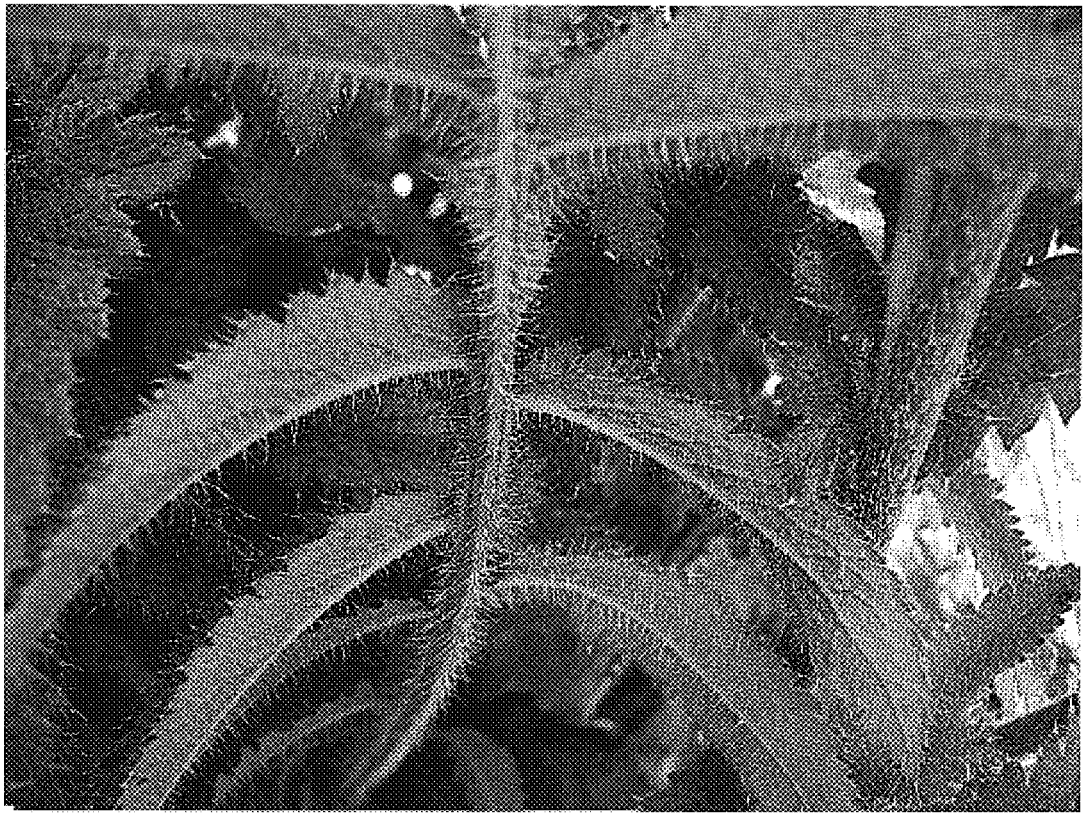
FIG. 1 shows the both sides of the leaves and the stems of the Plant.
Figure 2:
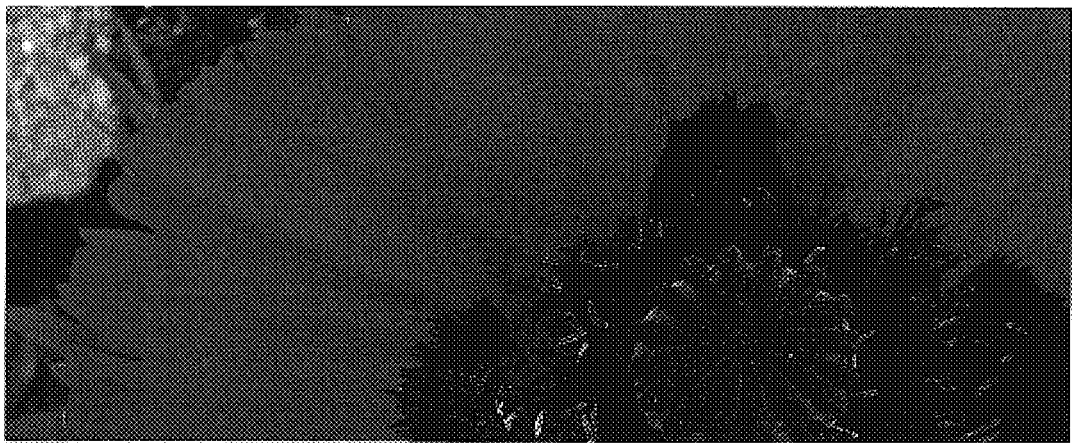
FIG. 2 shows the inside of the petals, stamens, pistils and superior ovary.
Figure 3:
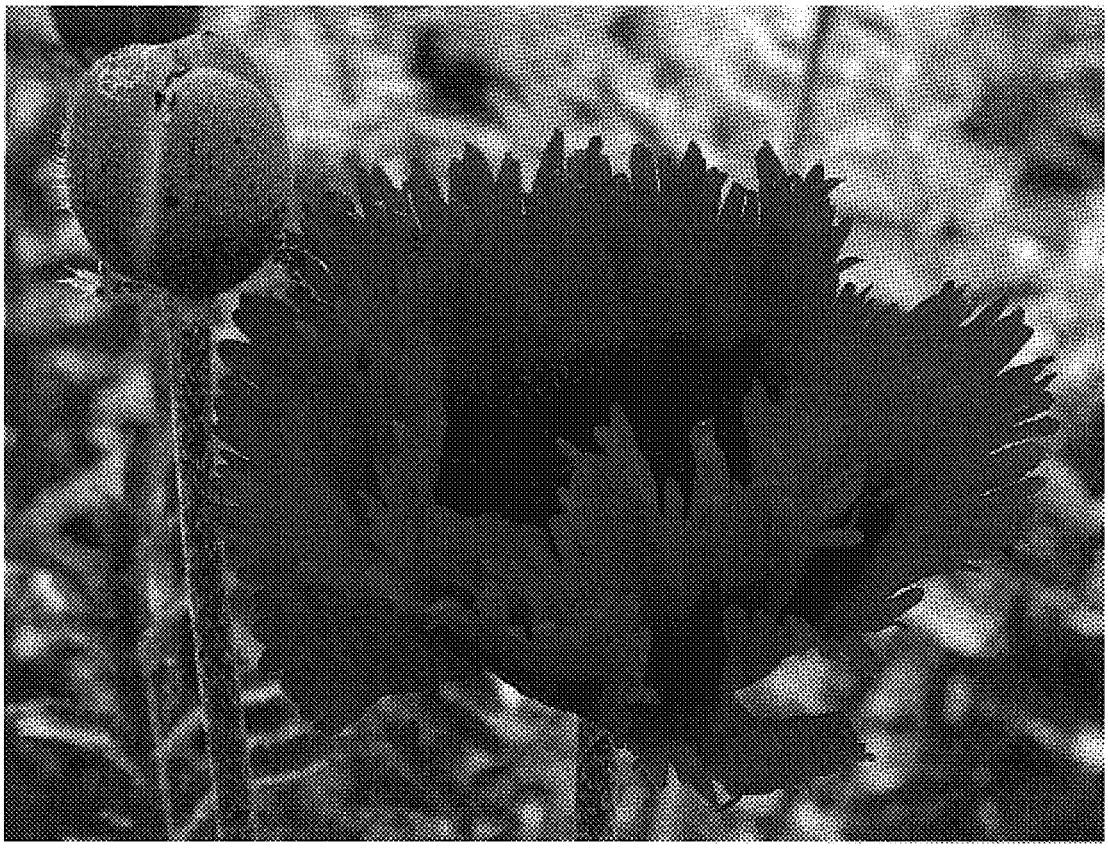
FIG. 3 shows the bud and flower from the side with intensely praemorse fringed petals.

The following description is based on a two-year old plant growing in a full-sun trial garden in Zeeland, Mich., USA. For the growing season up to the time of description the daytime temperatures range between 12–28° C., and night temperatures range between 5–18° C. Except for ordinary dictionary color usage, color references are according to The Royal Horticultural Society Colour Chart, 2001 edition.

Botanical classification: *Papaver orientale* L. cultivar 'Flamenco Dancer'.
Parentage: non-induced mutation of 'Turkenlouise'.
Asexual propagation: Root cuttings.
Time to initiation roots: 60 days; Time to finish as number 1 field grown, 9 months.
Plant habit: Basally branched rosette, rounded, with stems arising from base; 100 to 108 cm wide, 66 to 72 cm tall, leaves decreasing in size going up the stem with last 12 to 15 cm of stem void of leaves; up to 35 flowers per plant.
Leaves: Basally arranged; deeply lobed with lobes up to 10 cm long and 2.5 cm wide, hirsute to pubescent on upper and lower surfaces; Lowest leaves up to 45 cm long and 17 cm wide with about nine sets of lobes; pinnate with individual lobes dentate, veins netted. Apex acute; base cuneate; Petiole up to 1.5 cm wide and 6 cm long; petiole color between RHS 138C and 138D in center on both sides and nearest RHS 139C on the edges of both sides. Leaf color: top surface RHS 141A, lower surface RHS 139D; Veins on top darker than RHS 141A and bottom veins lighter than RHS 139D.
Flower: Single, one per stem, cupped, upward facing, mostly five petaled,
Fragrance: Not detected;
Flowering period: Mid to May through late June;
Flower size: 16 to 19 cm across and 5 to 6 cm tall.

Flower longevity: 3 to 4 days

Flower buds: One day before showing color –3.5 to 4.0 cm and 2.0 to 2.5 cm diameter; ovoid pubescent to hirsute; with three fugacious scales covering the bud nearest RHS 138B;

Peduncle: 8 mm wide at base and erect up to 72 cm tall, with mostly adpressed, densely pubescent white hairs to 4 mm long; color: RHS 138A Petals: Glabrous on both surfaces, 8 to 9 cm long and 9 to 10 cm wide; rounded, deeply praemorse, fringed apex, incised up to 2 cm deep; color of both surfaces between RHS 44A and RHS 44B; solid basal patches up to 3 cm wide and 1.8 cm deep on each petal, distal section closest to RHS N186B and most proximal section nearest RHS N34A on inner surface, and striated veined section on the outside of the same dimension, veins of RHS 187B.

Sepals: Mostly three, pubescent, pinnatifid, to 2.5 cm long and 1.5 cm wide, acute margin; ovate base; upper and lower surfaces RHS 138C in the center and RHS 137D toward the outside.

Reproductive organs:

*Gynoecium.*—Pistil — one, ovoid with flattened head, about 3.5 cm tall and 3.0 cm in diameter, RHS 138C; Stigma 15 to 18 radiating from center of flattened head, 1.5 cm long and 2 to 3 mm wide, RHS N186C.

*Androecium.*—Stamens: numerous, about 250, about 2.3 cm long, narrow to less than 1 mm in diameter, RHS 187A; Anther: 3 mm long and 1 mm wide, RHS 187A before dehiscing; internally with lighter parts of RHS 159B; Pollen: fine, minute, RHS N187B.

Fruit: Dehiscent capsule, 3.5 cm tall and 3.0 cm in diameter; between RHS N138B and RHS N138C;

Seeds: rounded; less than 1 mm in diameter; numerous, about 1000 per fruit; between RHS 202A and RHS N200A. 'Flamenco Dancer' is tolerant of winter temperatures as low as –25° C. and summer temperatures of 40° C. Tends to die back to the ground after flowering and leaf out again after a short resting period of about a month. Tolerant of dry summer conditions but does best with ample moisture in spring.

Not known to be tolerant of diseases and pest that are common to other *Papaver* cultivars.

I claim:

1. The new and distinct cultivar of *Papaver orientale* plant named 'Flamenco Dancer' as described and illustrated, with deeply fringed red petals and upright cupped flowers.

* * * * *